United States Patent
Choi et al.

(10) Patent No.: US 11,622,692 B2
(45) Date of Patent: Apr. 11, 2023

(54) SIGNAL PROCESSING APPARATUS, AND APPARATUS AND METHOD FOR ESTIMATING BIO-INFORMATION

(71) Applicant: SAMSUNG ELECTRONICS CO., LTD., Suwon-si (KR)

(72) Inventors: Chang Mok Choi, Suwon-si (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 316 days.

(21) Appl. No.: 16/904,732

(22) Filed: Jun. 18, 2020

(65) Prior Publication Data

US 2021/0235996 A1 Aug. 5, 2021

(30) Foreign Application Priority Data

Jan. 30, 2020 (KR) .................. 10-2020-0010772

(51) Int. Cl.
| | | |
|---|---|---|
| *A61B 5/0205* | (2006.01) | |
| *A61B 5/02* | (2006.01) | |
| *A61B 5/16* | (2006.01) | |
| *A61B 5/00* | (2006.01) | |
| *A61B 5/021* | (2006.01) | |

(Continued)

(52) U.S. Cl.
CPC ........ *A61B 5/0205* (2013.01); *A61B 5/02007* (2013.01); *A61B 5/165* (2013.01); *A61B 5/6843* (2013.01); *A61B 5/7203* (2013.01); *A61B 5/725* (2013.01); *A61B 5/7257* (2013.01); *A61B 5/02108* (2013.01); *A61B 5/02225* (2013.01); *A61B 5/02416* (2013.01); *A61B 5/0535* (2013.01)

(58) Field of Classification Search
CPC ..... A61B 5/7203; A61B 5/725; A61B 5/7257; A61B 5/02108; A61B 5/02225; A61B 5/02416; A61B 5/0535; A61B 5/0295
See application file for complete search history.

(56) References Cited

U.S. PATENT DOCUMENTS

| | | |
|---|---|---|
| 7,232,412 B2 | 6/2007 | Shirasaki et al. |
| 8,784,325 B2 | 7/2014 | Kim et al. |

(Continued)

FOREIGN PATENT DOCUMENTS

| | | | |
|---|---|---|---|
| EP | 3 087 915 A1 | 11/2016 | |
| EP | 3403574 A1 * | 11/2018 | ......... A61B 5/02108 |

(Continued)

OTHER PUBLICATIONS

Wendy Van Moer et al. "Linearizing Oscillometric Blood-Pressure Measurements: (Non)Sense?" IEEE Transactions on Instrumentation and Measurement, vol. 60, No. 4, Apr. 2011, (pp. 1267-1275).

(Continued)

*Primary Examiner* — Brian T Gedeon
(74) *Attorney, Agent, or Firm* — Sughrue Mion, PLLC

(57) ABSTRACT

A signal processing apparatus includes a memory configured to store instructions; and a processor configured to execute the instructions to obtain a signal; obtain a frequency band spectrum by applying a Fast Fourier Transform (FFT) to the obtained signal; and remove noise from the obtained spectrum by applying a first filter and a second filter, which are different from each other, to the obtained frequency band spectrum.

20 Claims, 14 Drawing Sheets

(51) Int. Cl.
*A61B 5/022* (2006.01)
*A61B 5/024* (2006.01)
*A61B 5/0535* (2021.01)

(56) References Cited

U.S. PATENT DOCUMENTS

| | | | |
|---|---|---|---|
| 9,241,671 B2 | 1/2016 | Hwang et al. | |
| 9,855,012 B2 | 1/2018 | Banerjee et al. | |
| 10,242,854 B2 | 3/2019 | Rusinov et al. | |
| 10,575,780 B2 | 3/2020 | van den Ende et al. | |
| 2009/0209868 A1* | 8/2009 | Hersh | A61B 5/02225 600/485 |
| 2013/0085354 A1* | 4/2013 | Hete | A61B 5/0205 600/323 |
| 2014/0276119 A1* | 9/2014 | Venkatraman | A61B 5/02405 600/509 |
| 2015/0105666 A1 | 4/2015 | Strachan | |
| 2017/0143272 A1 | 5/2017 | Brouse | |
| 2017/0347901 A1 | 12/2017 | Shao et al. | |
| 2018/0055427 A1* | 3/2018 | Chase | A61B 5/6826 |
| 2018/0184983 A1 | 7/2018 | Petersen et al. | |
| 2018/0317852 A1* | 11/2018 | MacDonald | A61B 5/7246 |
| 2019/0076032 A1* | 3/2019 | Park | A61B 5/02438 |
| 2020/0015688 A1 | 1/2020 | Li et al. | |
| 2020/0015690 A1 | 1/2020 | Choi et al. | |

FOREIGN PATENT DOCUMENTS

| | | | |
|---|---|---|---|
| JP | 2000-217796 A | 8/2000 | |
| JP | 6546661 B2 | 7/2019 | |
| KR | 10-1008825 B1 | 1/2011 | |
| KR | 10-1426591 B1 | 8/2014 | |
| KR | 10-2018-0067348 A | 6/2018 | |
| KR | 10-2020-0054723 A | 5/2020 | |
| KR | 10-2020-0097143 A | 8/2020 | |
| WO | 2013/179020 A1 | 12/2013 | |
| WO | WO-2015123753 A1 * | 8/2015 | A61B 5/0024 |
| WO | 2016/083074 A1 | 6/2016 | |
| WO | 2016/096391 A1 | 6/2016 | |

OTHER PUBLICATIONS

Communication dated Jan. 20, 2021 by the European Patent Office in counterpart European Patent Application No. 20186833.8.

* cited by examiner

SIGNAL PROCESSING APPARATUS, AND APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2020-0010772, filed on Jan. 30, 2020, in the Korean Intellectual Property Office, the disclosure of which is incorporated by reference herein in its entirety.

BACKGROUND

1. Field

The disclosure relates to signal processing technology and technology for estimating bio-information by using the same.

2. Description of Related Art

Generally, methods of non-invasively measuring blood pressure without damaging a human body include a method to measure blood pressure by measuring a cuff-based pressure, and a method to estimate blood pressure by measuring pulse waves without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a pressure signal changes significantly.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

Additional aspects will be set forth in part in the description which follows and, in part, will be apparent from the description, or may be learned by practice of the presented embodiments.

In accordance with an aspect of an example embodiment, a signal processing apparatus includes a memory configured to store instructions; and a processor configured to execute the instructions to obtain a signal; obtain a frequency band spectrum by applying a Fast Fourier Transform (FFT) to the obtained signal; and remove noise from the obtained spectrum by applying a first filter and a second filter, which are different from each other, to the obtained frequency band spectrum.

The first filter may include a Gaussian-based asymmetric window filter, and the second filter may include a Gaussian-based symmetric window filter.

The processor may apply the first filter to a main frequency of the spectrum; and apply the second filter to harmonic frequencies of the frequency band spectrum.

Based on removing the noise from the frequency band spectrum, the processor may recover the signal by applying an inverse FFT to the spectrum.

According to an aspect of an example embodiment, an apparatus for estimating bio-information may include a sensor configured to obtain a bio-signal from an object; and a processor configured to obtain a frequency band spectrum by applying a Fast Fourier Transform (FFT) to the obtained bio-signal; remove noise from the obtained frequency band spectrum by applying a first filter and a second filter, which are different from each other, to the obtained frequency band spectrum; and estimate the bio-information based on the frequency band spectrum from which the noise is removed.

The bio-signal may include at least one of a photoplethysmogram (PPG) signal, an impedance plethysmogram (IPG) signal, a pressure wave signal, and a video plethysmogram (VPG) signal.

The first filter may include a Gaussian-based asymmetric window filter, and the second filter may include a Gaussian-based symmetric window filter.

The processor may apply the first filter to a main frequency of the obtained frequency band spectrum, and apply the second filter to harmonic frequencies of the obtained frequency band spectrum.

The processor may recover the bio-signal by applying an inverse FFT to the frequency band spectrum from which the noise is removed.

The processor may extract an oscillometric peak from the recovered bio-signal, and estimate the bio-information based on the extracted oscillometric peak.

The apparatus may include a contact pressure sensor configured to measure contact pressure between the object and the sensor. The processor may estimate the bio-information based on the oscillometric peak and the measured contact pressure.

The bio-information may include at least one of blood pressure, vascular age, arterial stiffness, aortic pressure waveform, vascular compliance, stress index, and fatigue level.

According to an aspect of an example embodiment, a method of estimating bio-information may include obtaining a bio-signal from an object; obtaining a frequency band spectrum by applying a Fast Fourier Transform (FFT) to the obtained bio-signal; removing noise from the obtained frequency band spectrum by applying a first filter and a second filter, which are different from each other, to the obtained frequency band spectrum; and estimating bio-information based on the frequency band spectrum from which the noise is removed.

The first filter may include a Gaussian-based asymmetric window filter, and the second filter may include a Gaussian-based symmetric window filter.

The removing of the noise may include applying the first filter to a main frequency of the obtained frequency band spectrum; and applying the second filter to harmonic frequencies of the obtained frequency band spectrum.

The method may include recovering the bio-signal by applying an inverse FFT to the spectrum from which the noise is removed.

The estimating of the bio-information may include extracting an oscillometric peak from the recovered bio-signal, and estimating the bio-information based on the extracted oscillometric peak.

The method may include measuring contact pressure applied to the object while the bio-signal is obtained, and the estimating of the bio-information may include estimating the bio-information based on the oscillometric peak and the measured contact pressure.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
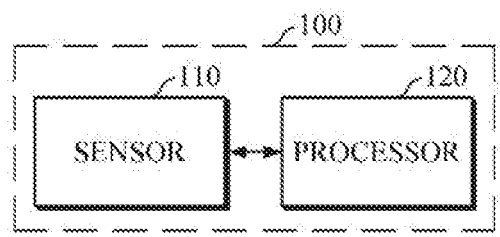
FIG. 1 is a block diagram illustrating a signal processing apparatus according to an embodiment.

Details of the embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. The term "comprising" may imply the inclusion of the stated elements, and might not preclude the inclusion of additional elements. In the following description, terms such as "unit" and "module" indicate a unit for processing at least one function or operation and they may be implemented by using hardware, software, or a combination thereof.

Hereinafter, embodiments of a signal processing apparatus and signal processing method, and an apparatus and method for estimating bio-information will be described in detail with reference to the accompanying drawings.

Referring to FIG. 1, a signal processing apparatus 100 includes a sensor 110 and a processor 120. FIGS. 2A to 2F are diagrams explaining examples of Gaussian-based filtering.

The sensor 110 may obtain various bio-signals, such as photoplethysmogram (PPG) signals, impedance plethysmogram (IPG) signals, pressure wave signals, video plethysmogram (VPG) signals, electrocardiogram (ECG) signals, ballistocardiogram (BCG) signals, and the like. The processor 120 may receive the bio-signals from the sensor 110.

In another example, the processor 120 may receive signals from an external device by controlling a communication module mounted in the signal processing apparatus 100. In this case, examples of the external device may include a smartphone, a tablet personal computer (PC), a laptop computer, and a desktop computer, which may be used for processing various signals, as well as devices in medical institutions.

The processor 120 may remove noise by processing the signal obtained by the sensor 110. The processor 120 may obtain a frequency band spectrum by applying a Fast Fourier Transform (FFT) to the signal.

The processor 120 may remove noise from the spectrum by applying a first filter and a second filter, which are Gaussian-based filters and different from each other, to the obtained frequency band spectrum. In this case, the first filter may be a Gaussian-based asymmetric window filter, and the second filter may be a Gaussian-based symmetric window filter. The processor 120 may apply the first filter to a main frequency of the frequency band spectrum, and may apply the second filter to a harmonic frequency of the spectrum.

Figure 2A:
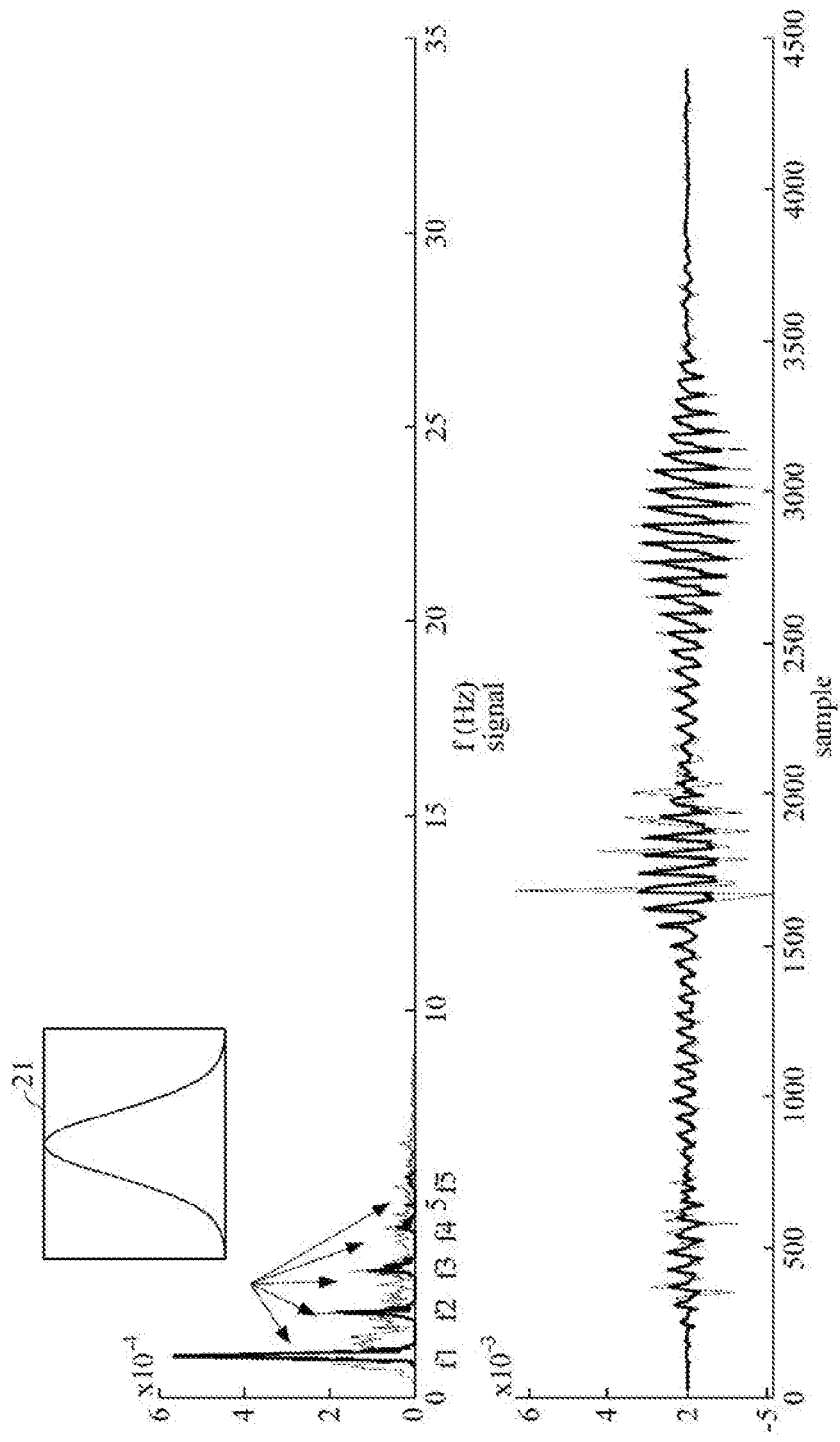
FIGS. 2A to 2F are diagrams explaining examples of Gaussian-based filtering according to an embodiment.

FIG. 2A is a diagram explaining an example of applying a Gaussian symmetric window 21. A lower graph of FIG. 2A shows an original signal (light line) and a signal (dark line) which is recovered after filtering. Further, an upper graph of FIG. 2A shows a frequency band spectrum (light line in the upper graph) which is obtained by applying an FFT to the original signal (light line in the lower graph). As illustrated in FIG. 2A, by applying an equal-sized Gaussian symmetric window 21 to a main frequency f1 and harmonic frequencies f2, f3, f4, and f5 of the frequency band spectrum (light line in the upper graph) and by recovering the signal by applying an inverse FFT thereto, noise may be removed effectively as shown in the recovered signal of the lower graph (dark line in the lower graph).

Figure 2B:
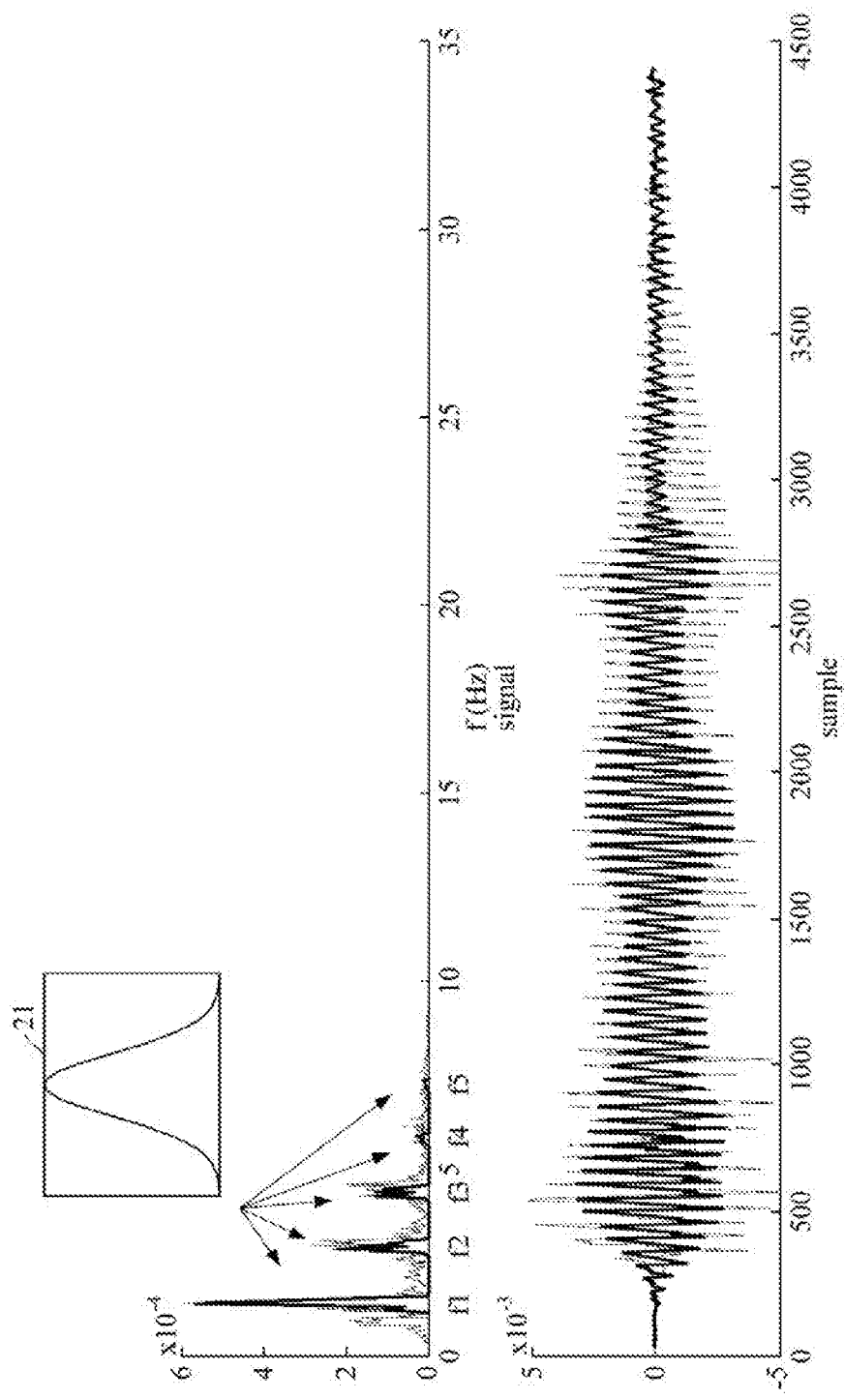

FIG. 2B is a diagram illustrating an example of applying a symmetric window 21, having a relatively small size, to a main frequency 1 and harmonic frequencies f2, f3, f4, and f5 of a frequency band spectrum (light line in an upper graph) by applying an FFT to an original signal (light line in a lower graph). As illustrated in FIG. 2B, when a Gaussian-based symmetric window having a relatively small window size is applied, information of the original signal may not be retrieved properly, such that the original signal may be reduced while noise is removed effectively.

Figure 2C:
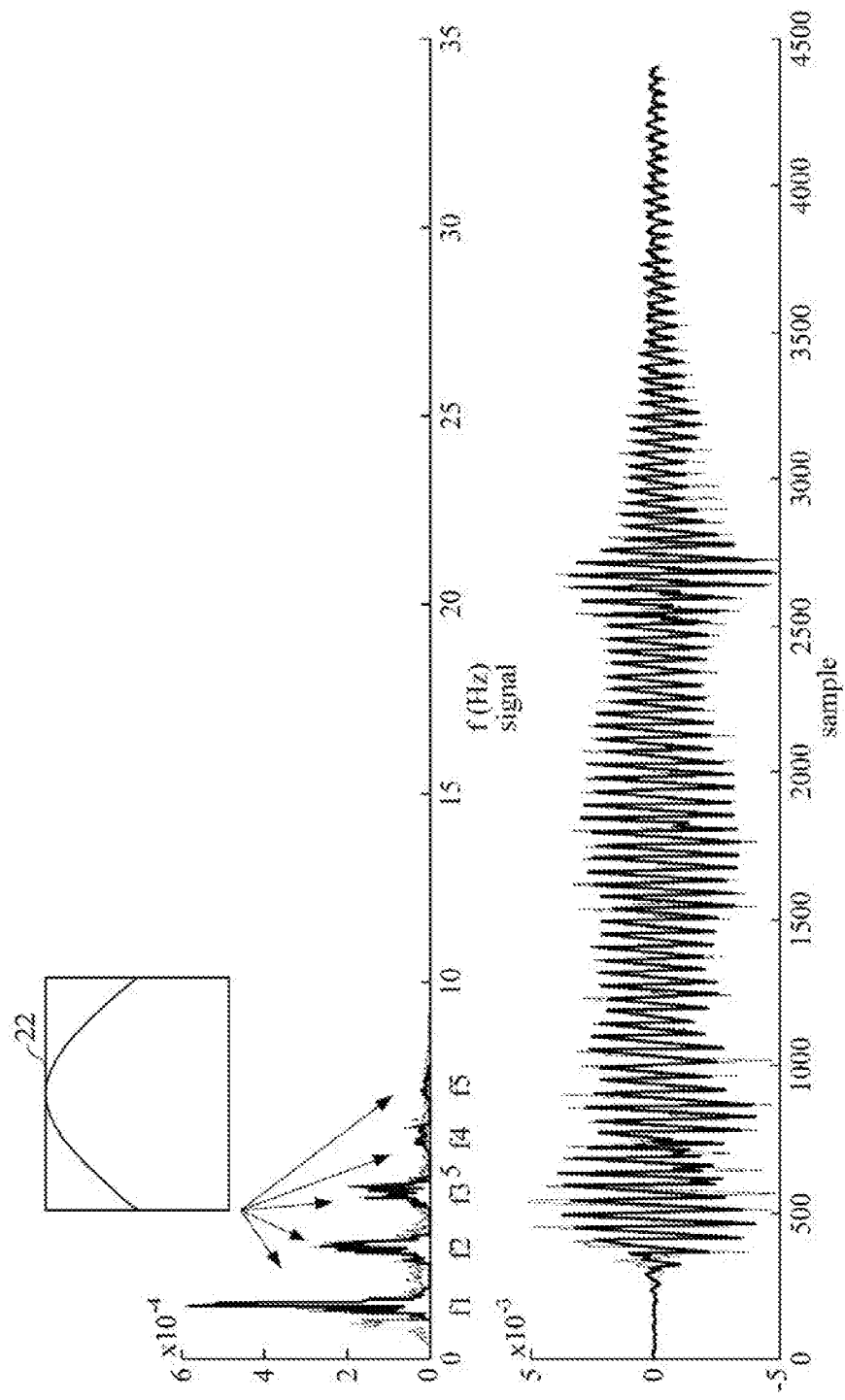
Figure 2D:
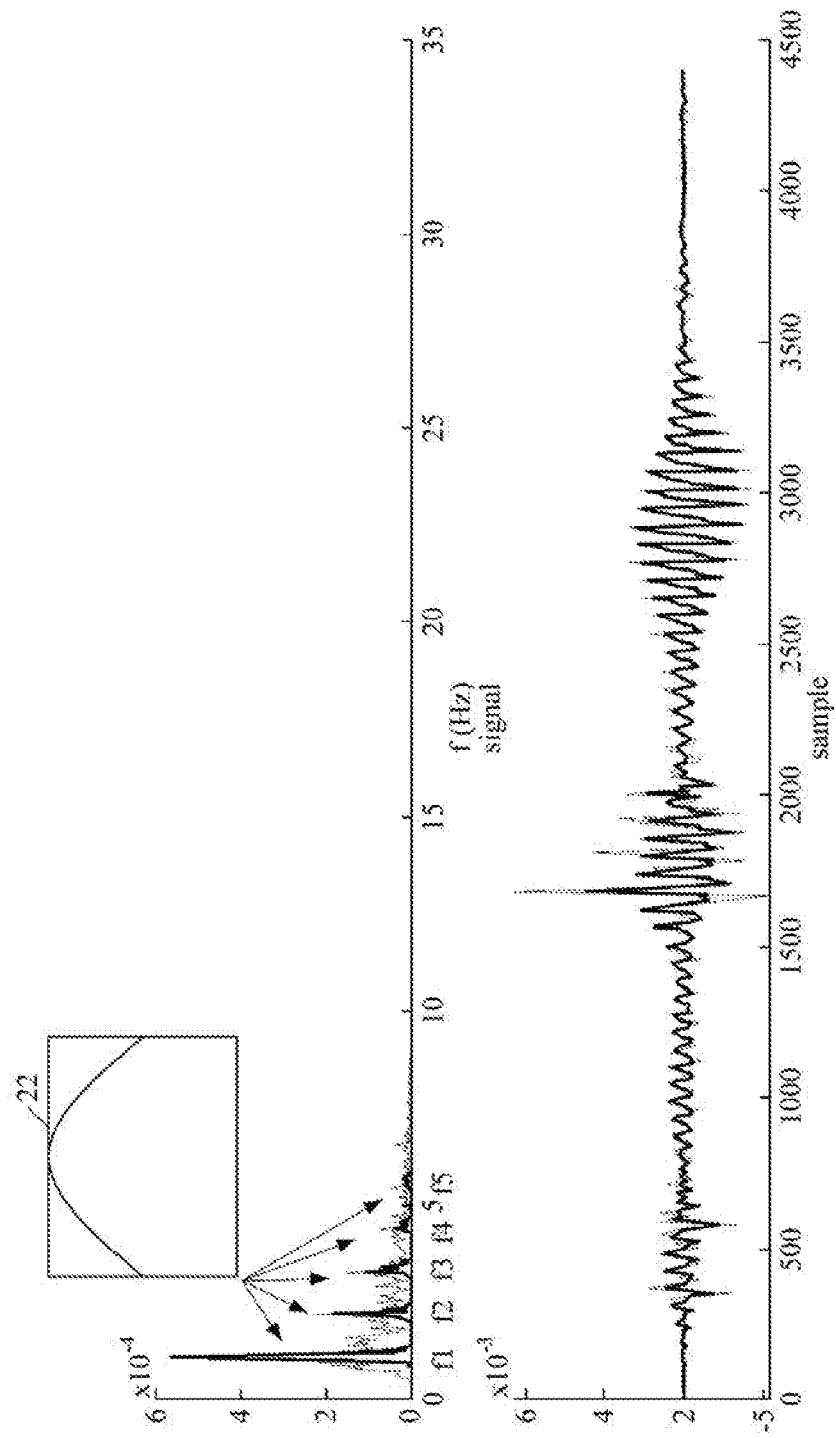

FIGS. 2C and 2D are diagrams illustrating an example of applying a symmetric window 22, having a relatively large size, to a main frequency 1 and harmonic frequencies f2, f3, f4, and f5 of a frequency band spectrum (light line in an upper graph) by applying an FFT to an original signal (light line in a lower graph). As illustrated in FIGS. 2C and 2D, when a Gaussian-based symmetric window with a larger window size is applied, the problem of reducing the original signal may be solved. However, referring to FIG. 2D, if a window size is increased, noise may not be removed effectively while the problem of reducing the original signal is reduced.

Figure 2E:
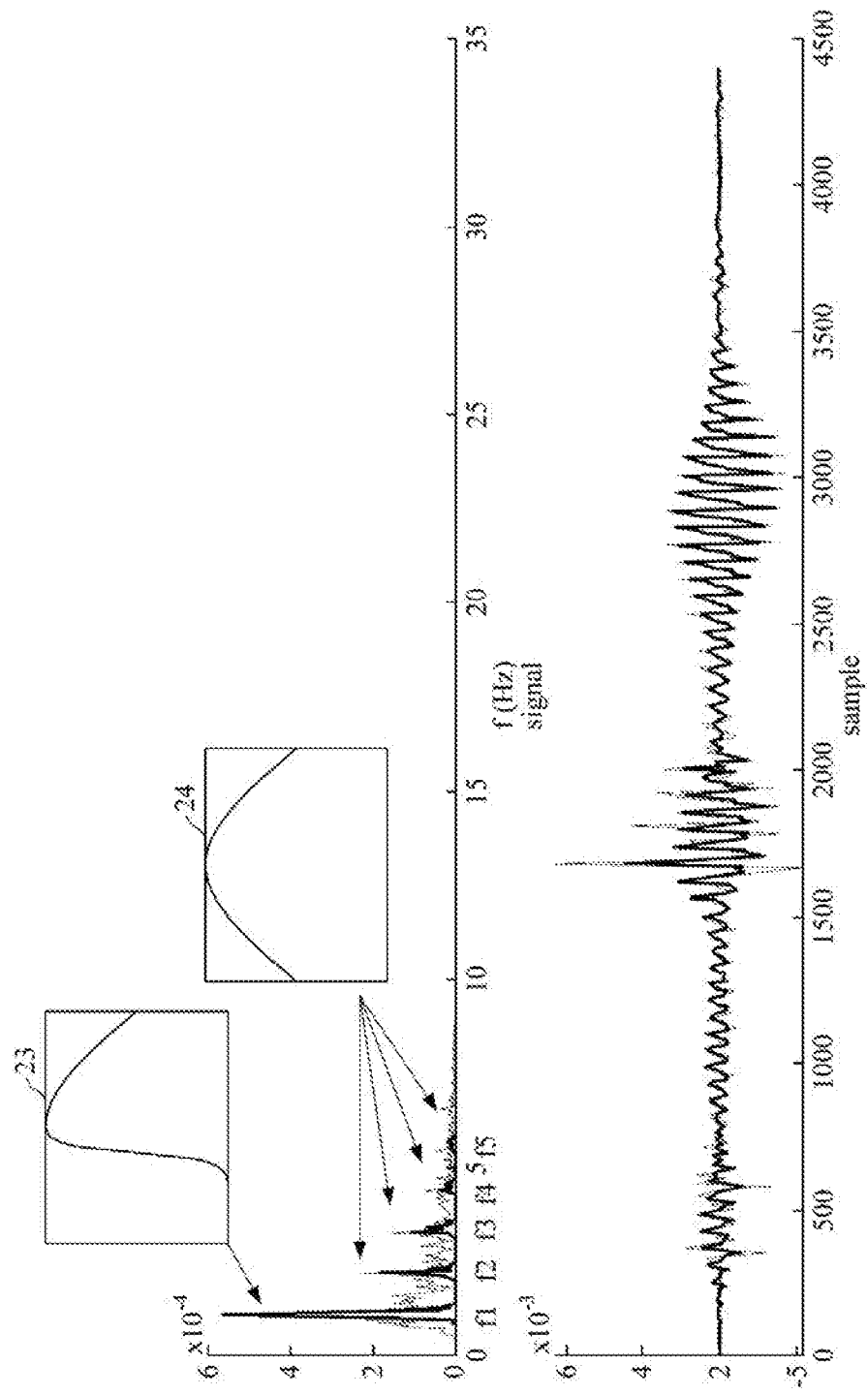
Figure 2F:
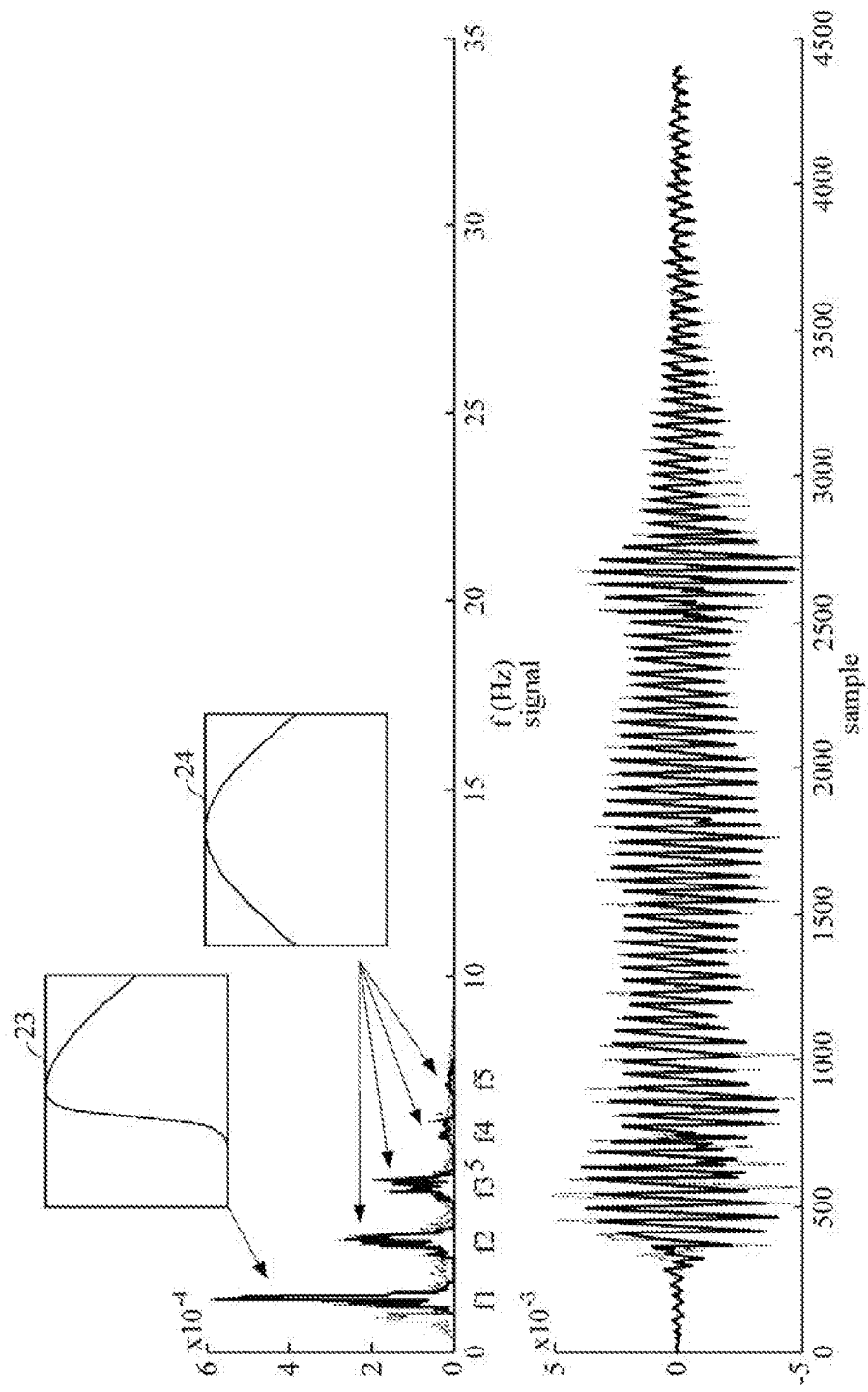

FIGS. 2E and 2F illustrate an example of applying two different filters 23 and 24 to a spectrum (light line in an upper graph) which is obtained from an original signal (light line in a lower graph) by applying an FFT. In this case, one filter 23 is a Gaussian-based asymmetric window filter, and the other one 24 is a Gaussian-based symmetric window filter. In this case, a degree of asymmetry may be pre-defined by considering a type of the obtained signal, computing performance, accuracy in analysis, a type of bio-information to be estimated, and the like. As illustrated in FIGS. 2E and 2F, the asymmetric window may be applied to a main frequency f1 of the spectrum, and the symmetric window may be applied to harmonic frequencies f2, f3, f4, and f5 of the spectrum. By applying the asymmetric window to the spectrum, a signal (dark line in the lower graph) may be recovered, from which noise is removed effectively, while maintaining the original signal.

Figure 3:
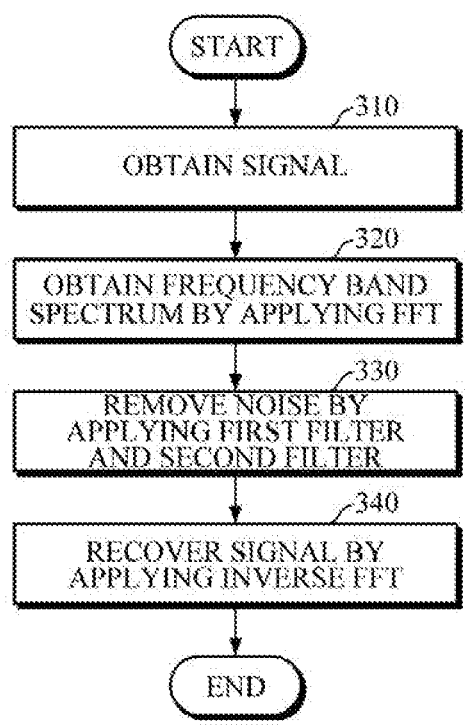
FIG. 3 is a flowchart illustrating a signal processing method according to an embodiment.

FIG. 3 is a flowchart illustrating a signal processing method according to an embodiment of the present disclosure. The method of FIG. 3 is an example of a signal processing method performed by the signal processing apparatus 100 of FIG. 1.

The signal processing apparatus 100 may obtain a signal to be processed in operation 310. The signal processing apparatus 100 may receive the signal from a signal measuring sensor, mounted inside or outside thereof, or from a smartphone, a tablet PC, a device in a medical institution, and the like.

Then, the signal processing apparatus 100 may obtain a frequency band spectrum by applying an FFT to the obtained signal in operation 320, and may remove noise by applying two different filters to the obtained spectrum in operation 330. In this case, the filters are Gaussian-based filters, in which one may be an asymmetric window and the other one may be a symmetric window. The signal processing apparatus 100 may apply the asymmetric window to a main frequency of the spectrum, and may apply the symmetric window to harmonic frequencies of the spectrum.

Subsequently, the signal processing apparatus 100 may recover the signal by applying an inverse FFT to the spectrum, from which noise is removed, in operation 340.

Figure 4:
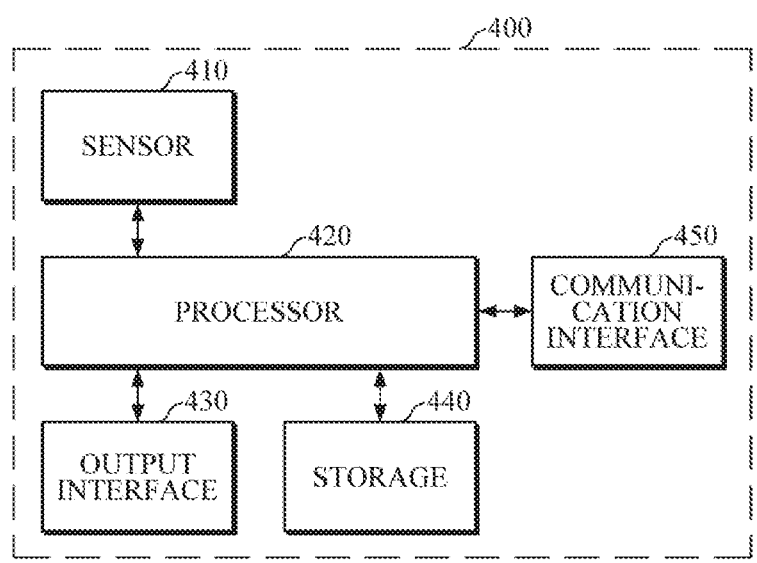
FIG. 4 is a block diagram illustrating an apparatus for estimating bio-information according to an embodiment.
Figure 5:
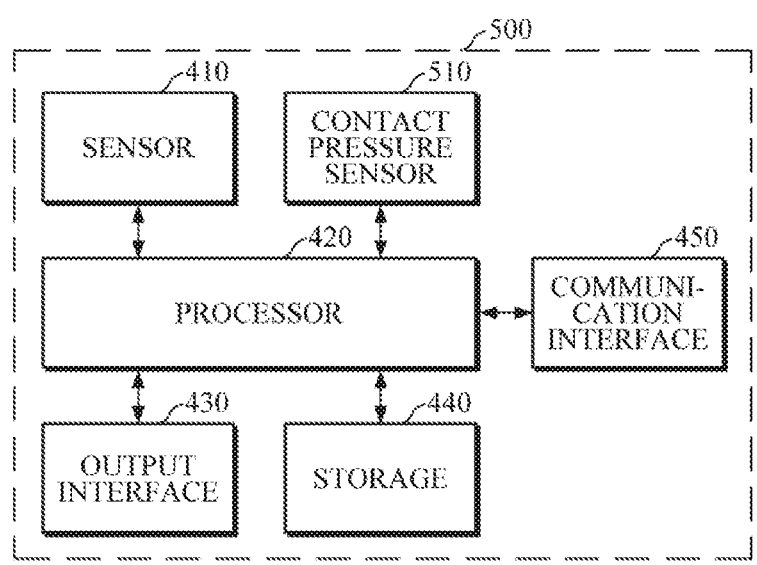
FIG. 5 is a block diagram illustrating an apparatus for estimating bio-information according to another embodiment.

FIG. 4 is a block diagram illustrating an apparatus for estimating bio-information according to an embodiment of the present disclosure. FIG. 5 is a block diagram illustrating an apparatus for estimating bio-information according to another embodiment of the present disclosure. The functions of the aforementioned signal processing apparatus 100 may be embedded in apparatuses 400 and 500 for estimating bio-information.

Referring to FIG. 4, the apparatus 400 for estimating bio-information includes a sensor 410, a processor 420, an output interface 430, a storage 440, and a communication interface 450.

The sensor 410 may obtain a bio-signal from an object. For example, the sensor 410 may include a pulse wave sensor for acquiring PPG signals from the object. However, the sensor 410 is not limited thereto, and may include sensors for acquiring various bio-signals such as IPG signals, pressure wave signals, VPG signals, ECG signals, BCG signals, and the like. In this case, the object may be skin tissue of the human body and may be, for example, a body part such as the back of a hand, a wrist, a finger, and the like, at which veins or capillaries are located. However, the object is not limited thereto, and may be a body part at which arteries, such as the radial artery, are located.

The sensor 410 may include a light source which emits light onto the object, and a detector which detects light scattered by or reflected from the object. In this case, the light source may include a light-emitting diode (LED), a laser diode, a phosphor, and the like. Further, the detector may include a photo diode, an image sensor, and the like, but is not limited thereto. The light source and/or the detector may be formed as an array of two or more light sources and/or detectors, and each of the light sources may emit light of different wavelengths.

The processor 420 may be electrically connected to the sensor 410. In response to a request for estimating bio-information, the processor 420 may control the sensor 410, and may obtain bio-information by using a bio-signal received from the sensor 410. In this case, bio-information may include blood pressure, vascular compliance, cardiac output, total peripheral resistance, vascular age, and the like.

Based on receiving the bio-signal, the processor 420 may perform preprocessing to remove noise. The processor 420 may obtain a frequency band spectrum by applying an FFT to the bio-signal. Further, the processor 420 may remove noise from the spectrum by applying two or more different Gaussian-based filters to the spectrum, and may recover the bio-signal by applying an inverse FFT. For example, one of the different filters may be an asymmetric window and the other one may be a symmetric window. In this case, the processor 420 may apply the asymmetric window to a main frequency of the frequency band spectrum, and may apply the symmetric window to harmonic frequencies of the spectrum.

Based on recovering the pulse wave signal, the processor 420 may extract an oscillometric peak from the recovered signal. Based on extracting the oscillometric peak, the processor 420 may extract time and/or amplitude values of the oscillometric peak, as well as time and/or amplitude values corresponding to a predetermined ratio (e.g., 0.5 to 0.7) to the amplitude value of the oscillometric peak, or time and/or amplitude values at points before and after the peak point, and at which a slope is maximum/minimum, and the like as additional features. The processor 420 may estimate blood pressure by applying a blood pressure estimation model which defines a correlation between the extracted features and blood pressure. Alternatively, the processor 420 may estimate blood pressure based on the extracted features and contact pressure between the object and the sensor 410.

For example, the processor 420 may obtain contact pressure based on an amplitude value at each time of the pulse wave signal by applying a contact pressure conversion model which defines a correlation between the amplitude and the contact pressure. The processor 420 may independently estimate mean arterial pressure, systolic blood pressure, and diastolic blood pressure based on a contact pressure value corresponding to a time point of the oscillometric peak, and contact pressure values at the right and left time points corresponding to a predetermined ratio to the amplitude value of the oscillometric peak. In this case, the processor 420 may estimate blood pressure by using a blood pressure estimation model which defines a correlation between the contact pressure and blood pressure.

The output interface 430 may provide a variety of information, related to the estimated bio-information, for a user by using various output modules. In this case, the output modules may include a visual output module such as a display, and the like, a voice output module such as a speaker, and the like, or a haptic module, and the like, using vibrations, tactile sensation, and the like, but is not limited thereto. The output interface 430 may output information, such as an estimated blood pressure value and/or a user's health condition determined based on the estimated blood pressure value, an action in response to the determined health condition, and the like. Further, the output interface 430 may output a blood pressure estimation history in the form of graphs, and may provide detailed information related to estimating blood pressure at a corresponding time point selected by a user.

The storage 440 may store reference information related to estimating bio-information, the pulse wave signal, the estimated bio-information value, the extracted feature information, and the like. In this case, the reference information may include information, such as user characteristic information including a user's age, sex, health condition, and the like, reference blood pressure, a bio-information estimation model, a contact pressure conversion model, and the like.

The storage 440 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static RAM (SRAM), a Read Only Memory (ROM), an Electrically Erasable Programmable ROM (EEPROM), a Programmable ROM (PROM), a magnetic memory, a magnetic disk, and an optical disk, and the like, but is not limited thereto.

The communication interface 450 may communicate with an external device by using the communication modules as described above, and may transmit and receive a variety of information to and from the connected external device. In this case, examples of the external device may include a blood pressure measuring device such as a cuff manometer, a medical device related to measuring bio-information, and an information processing device such as a smartphone, a tablet PC, a desktop computer, a laptop computer, and the like. For example, the communication interface 450 may receive cuff blood pressure, a bio-information estimation model, a contact pressure conversion model, and the like from the external device. Further, the communication interface 450 may transmit information, such as the pulse wave signal measured by the sensor 410, the features extracted by the processor 520, the estimated bio-information value, and the like, to the external device.

The communication interface 450 may communicate with the external device by using various wired or wireless communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G), fourth generation (4G), and fifth generation (5G) communications, and the like. However, this is merely exemplary and is not intended to be limiting.

Referring to FIG. 5, an apparatus 500 for estimating bio-information includes the sensor 410, the processor 420, the output interface 430, the storage 440, the communication interface 450, and a contact pressure sensor 510. The sensor 410, the processor 420, the output interface 430, the storage 440, and the communication interface 450 are described above with reference to FIG. 4, such that a detailed description thereof will be omitted.

Based on receiving a request for estimating bio-information, the processor 420 may provide guide information on a contact state for a user via the output interface 430. For example, the processor 420 may provide guide information on a contact position of the sensor 410, which is to be contacted by the object, and/or contact pressure to be changed while a bio-signal is measured.

The contact pressure sensor 510 may measure a change in contact pressure applied by the object to the sensor 410 while the bio-signal is measured.

Based on the pulse wave signal, obtained by the sensor 410, and the contact pressure obtained by the contact pressure sensor 510, the processor 420 may obtain an oscillometric envelope which indicates a correlation between an amplitude at each time of the pulse wave signal and the contact pressure. Further, the processor 420 may obtain the above features from the oscillometric envelope, and may estimate bio-information by using the obtained features.

Generally, if noise is included in the pulse wave signal due to motion noise of the object when the pulse wave signal is measured, an oscillometric peak may be erroneously detected from the pulse wave signal. However, in an embodiment of the present disclosure, an optimal (or improved) signal, from which noise is removed, may be recovered by applying a Gaussian-based asymmetric window to a frequency band spectrum, such that an oscillometric peak may be detected accurately.

Figure 6:
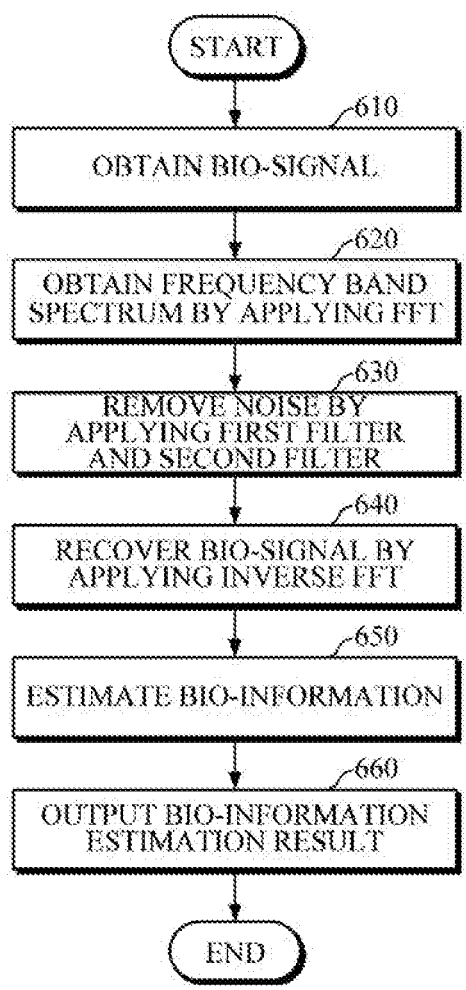
FIG. 6 is a flowchart illustrating a method of estimating bio-information according to an embodiment.

FIG. 6 is a flowchart illustrating a method of estimating bio-information according to an embodiment of the present disclosure. The method of FIG. 6 may be an example of a method of estimating bio-information which is performed by the apparatus 400 for estimating bio-information according to the embodiment of FIG. 4.

Based on receiving a request for estimating bio-information, the apparatus 400 for estimating bio-information may obtain a bio-signal in operation 610.

Then, the apparatus 400 for estimating bio-information may obtain a frequency band spectrum by applying an FFT to the obtained bio-signal in operation 620, and may remove noise by applying a first filter and a second filter, which are Gaussian-based filters and different from each other, to the spectrum in operation 630. In this case, the first filter may be a Gaussian-based asymmetric window filter, and the second filter may be a Gaussian-based symmetric window filter. For example, the apparatus 400 for estimating bio-information may apply the asymmetric window to a main frequency of the spectrum, and may apply the symmetric window to harmonic frequencies of the spectrum. In this manner, the apparatus 400 for estimating bio-information may recover the bio-signal while removing noise effectively.

Then, based on removing the noise from the frequency band spectrum, the apparatus 400 for estimating bio-information may recover the bio-signal by applying an inverse FFT in operation 640, and may estimate bio-information by using the bio-signal in operation 650. For example, the apparatus 400 for estimating bio-information may obtain an oscillometric peak from the recovered bio-signal, may obtain additional features based on a peak amplitude, and may obtain bio-information by applying a bio-information estimation model which defines a correlation between the features and bio-information.

Subsequently, the apparatus 400 for estimating bio-information may output a bio-information estimation result in operation 660. For example, the apparatus 400 for estimating bio-information may visually output the bio-information estimation result, a health condition monitoring result based on the bio-information estimation result, and the like on a display. Alternatively, the apparatus 400 for estimating bio-information may output bio-information by various methods using a voice output module, such as a speaker, and the like, or a haptic module, and the like, using vibrations, tactile sensation, and the like.

Figure 7:
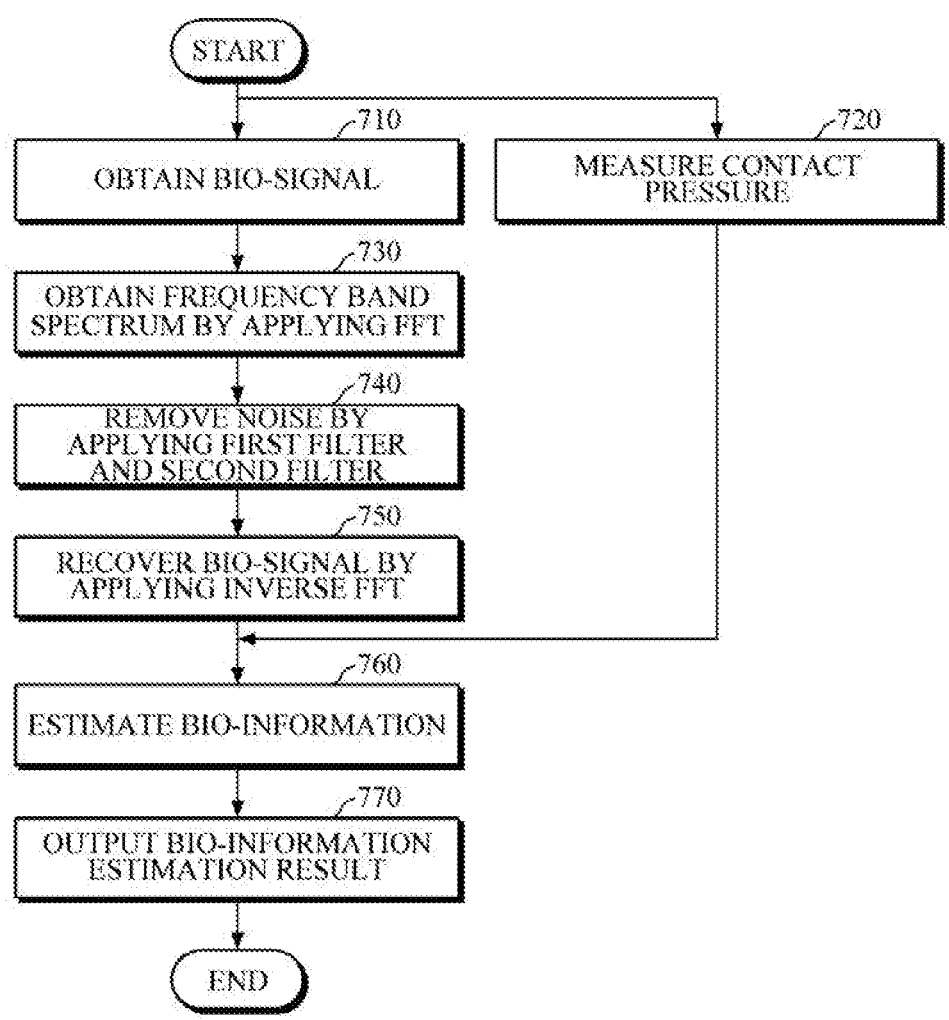
FIG. 7 is a flowchart illustrating a method of estimating bio-information according to another embodiment.

FIG. 7 is a flowchart illustrating a method of estimating bio-information according to another embodiment of the present disclosure. The method of FIG. 7 may be an example of a method of estimating bio-information which is performed by the apparatus 500 for estimating bio-information according to the embodiment of FIG. 5.

Based on receiving a request for estimating bio-information, the apparatus 500 for estimating bio-information may obtain a bio-signal by using a sensor in operation 710.

In this case, the apparatus 500 for estimating bio-information may measure contact pressure, applied to an object, by using a contact pressure sensor, while the bio-signal is measured, in operation 720.

Then, the apparatus 500 for estimating bio-information may obtain a frequency band spectrum by applying an FFT to the obtained bio-signal in operation 730, and may remove noise by applying Gaussian-based asymmetric and symmetric windows to the spectrum in operation 740. For example, the apparatus 500 for estimating bio-information may apply the asymmetric window to a main frequency of the spectrum, and may apply the symmetric window to harmonic frequencies of the spectrum. In this manner, the apparatus 500 for estimating bio-information may recover the bio-signal while removing noise effectively.

Subsequently, based on removing the noise, the apparatus 500 for estimating bio-information may recover the bio-signal by applying an inverse FFT in operation 750, may estimate bio-information by using the bio-signal in operation 760, and may output a bio-information estimation result in operation 770. For example, the apparatus 500 for estimating bio-information may obtain an oscillometric peak from the recovered bio-signal, may obtain additional features based on a peak amplitude, and may obtain bio-information by applying a bio-information estimation model which defines a correlation between the features and bio-information.

Figure 8:
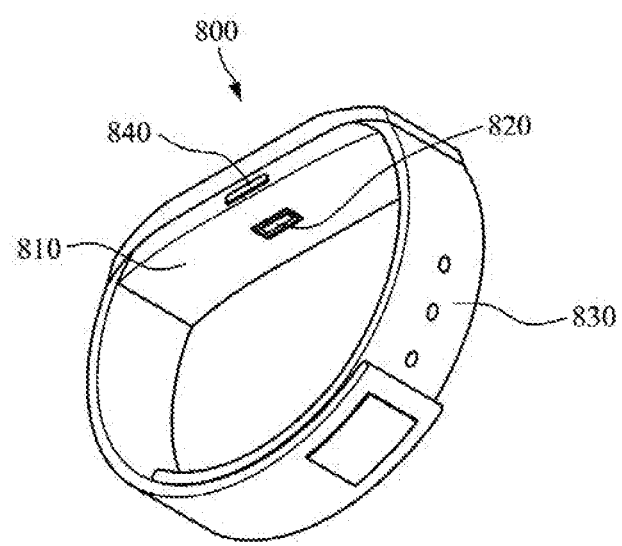
FIG. 8 is a diagram illustrating an example of a wearable device according to an embodiment.

FIG. 8 is a diagram illustrating a wearable device worn on an object. The aforementioned embodiments of the apparatuses 400 and 500 for estimating bio-information may be mounted in a smart watch worn on a user's wrist or a smart band type wearable device, but is not limited thereto.

Referring to FIG. 8, the wearable device 800 includes a main body 810 and a strap 830.

The main body 810 may be formed to have various shapes, and may include various modules which are mounted inside or outside of the main body 810 to perform the aforementioned functions of extracting features and estimating bio-information, as well as various other functions (e.g., time, alarm, etc.). A battery may be embedded in the main body 810 or the strap 830 to supply power to the various modules of the wearable device 800.

The strap 830 may be connected to the main body 810. The strap 830 may be flexible so as to be wrapped around a user's wrist. The strap 830 may be formed as a band that is detachable or un-detachable from the user's wrist. Air may be injected into the strap 830 or an airbag may be included in the strap 830, so that the strap 830 may have elasticity according to a change in pressure applied to the wrist, and may transmit the change in pressure of the wrist to the main body 810.

The main body 810 may include a sensor 820 for measuring a bio-signal. The sensor 820 may be mounted on one surface of the main body 810 which comes into contact with a user's wrist when the main body 810 is worn on the user's wrist. For example, the sensor 820 may include a light source for emitting light onto the wrist and a detector for detecting light scattered or reflected from body tissue such as a skin surface, blood vessels, and the like. However, the sensor 820 is not limited thereto.

In addition, a processor may be mounted in the main body 810, and may be electrically connected to various modules of the wearable device 800 to control operations thereof.

The processor may control the sensor 820 in response to a request for estimating bio-information. The request for estimating bio-information may be generated in response to a user's command input through a manipulator 840 or a touch screen of a display, or may be generated at predetermined bio-information estimation intervals or by monitoring a bio-information estimation result.

Based on the sensor 820 measuring the bio-signal, the processor may obtain a frequency band spectrum by applying an FFT to the obtained bio-signal, and may remove noise by applying Gaussian-based asymmetric and symmetric windows to the frequency band spectrum. In this case, the processor may apply the asymmetric window to a main frequency of the spectrum, and may apply the symmetric windows to a harmonic frequency of the spectrum. Further, the processor may recover the bio-signal by applying an inverse FFT to the spectrum, from which the noise is removed.

The processor may detect an oscillometric peak from the recovered bio-signal. In addition, the processor may obtain bio-information by using contact pressure applied to the object while measuring the oscillometric peak and the bio-signal.

The display may be mounted on a front surface of the main body 810, and may be a touch panel having a touch screen for sensing a touch input. The display may receive a user's touch input, may transmit the received touch input to the processor, and may display processing results of the processor. For example, the display may display a bio-information estimation result, and may display additional information, such as a bio-information estimation history, a change in health condition, warning information, and the like, along with the estimation result.

A storage, which stores the processing results of the processor and a variety of information, may be mounted in the main body 810. In this case, the variety of information may include information related to estimating bio-information, as well as information related to other functions of the wearable device 800.

In addition, the main body 810 may include a manipulator 840 which receives a user's command and transmits the received command to the processor. The manipulator 840 may include a power button to input a command to turn on/off the wearable device 800.

Moreover, a communication interface, which communicates with an external device, may be mounted in the main body 810. The communication interface may transmit a bio-information estimation result to an external device, so as to output the estimation result to the external device, e.g., an output module of a user's mobile terminal, or to store the estimation result in a storage module of the external device. Furthermore, the communication interface may receive information for supporting various other functions of the wearable device and the like from the external device.

Figure 9:
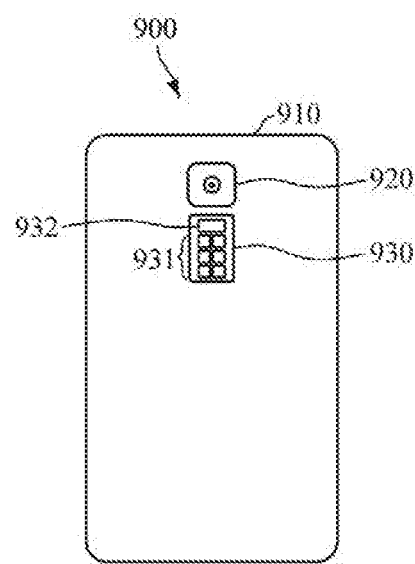
FIG. 9 is a diagram illustrating an example of a smart device according to an embodiment.

FIG. 9 is a diagram illustrating an example of a smart device. FIG. 9 illustrates a smart device, to which the embodiments of the above apparatuses 400 and 500 for estimating bio-information are applied. In this case, the smart device may be a smartphone and a tablet PC, but is not limited thereto.

Referring to FIG. 9, the smart device 900 may include a main body 910 and a sensor 930 mounted on one surface of the main body 910. The sensor 930 may include one or more light sources 931 and a detector 932. However, the sensor 930 is not limited thereto, and may include an impedance-based sensor or a pressure-based sensor. As illustrated in FIG. 9, the sensor 930 may be mounted on a rear surface of the main body 910, but is not limited thereto, and may be configured in combination with a fingerprint sensor or a touch panel mounted on a front surface of the main body 910.

A display may be mounted on a front surface of the main body 910. The display may visually display a bio-information estimation result and the like. The display may include a touch panel, and may receive information input through the touch panel and transmit the received information to the processor.

Moreover, an image sensor 920 may be mounted in the main body 910. When a user's finger approaches the sensor 930 to measure a bio-signal, the image sensor 920 may capture an image of the finger and may transmit the captured image to the processor. In this case, based on the image of the finger, the processor may identify a relative position of the finger with respect to an actual position of the sensor 930, and may provide the relative position of the finger for the user through the display, so as to guide the user to accurately contact the sensor 930 with the finger.

The processor may obtain a spectrum by applying an FFT to a bio-signal measured by the sensor 930, and may remove noise by applying Gaussian-based asymmetric and symmetric windows to the obtained spectrum. The processor may recover the bio-signal by applying an inverse FFT to the spectrum, from which the noise is removed, and may estimate bio-information by detecting a peak of an oscillometric envelope from the recovered bio-signal.

The processor may estimate bio-information, and may output the estimation result via the display.

The embodiments of the present disclosure may be implemented by computer-readable code stored on a on-transitory computer-readable medium. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium can be distributed over a plurality of computer systems connected to a network so that a computer-readable code is written thereto and executed therefrom in a decentralized manner. Functional programs, code, and code segments for implementing the embodiments of the present disclosure can be deduced by one of ordinary skill in the art.

The present disclosure has been described herein with regard to various embodiments. However, it will be obvious to those skilled in the art that various changes and modifications can be made without changing technical ideas and features of the present disclosure. Thus, it is clear that the above-described embodiments are illustrative in all aspects and are not intended to limit the present disclosure.

What is claimed is:

1. A signal processing apparatus comprising:
a memory configured to store instructions; and
a processor configured to execute the instructions to:
obtain a signal;
obtain a frequency band spectrum by applying a Fast Fourier Transform (FFT) to the obtained signal; and
remove noise from the obtained frequency band spectrum by applying a first filter and a second filter, which are different from each other, to the obtained frequency band spectrum;
wherein the first filter comprises an asymmetric window filter.

2. The signal processing apparatus of claim 1, wherein:
the asymmetric window filter comprises a Gaussian-based asymmetric window filter; and
the second filter comprises a Gaussian-based symmetric window filter.

3. The signal processing apparatus of claim 1, wherein the processor is further configured to:
apply the first filter to a main frequency of the frequency band spectrum; and
apply the second filter to harmonic frequencies of the frequency band spectrum.

4. The signal processing apparatus of claim 1, wherein based on removing the noise from the frequency band spectrum, the processor is further configured to recover the signal by applying an inverse FFT to the frequency band spectrum.

5. An apparatus for estimating bio-information, the apparatus comprising:
a sensor configured to obtain a bio-signal from an object; and
a processor configured to:
obtain a frequency band spectrum by applying a Fast Fourier Transform (FFT) to the obtained bio-signal;
remove noise from the obtained frequency band spectrum by applying a first filter and a second filter, which are different from each other, to the obtained frequency band spectrum; and
estimate the bio-information based on the frequency band spectrum from which the noise is removed;
wherein the first filter comprises an asymmetric window filter.

6. The apparatus of claim 5, wherein the bio-signal comprises at least one of a photoplethysmogram (PPG) signal, an impedance plethysmogram (IPG) signal, a pressure wave signal, and a video plethysmogram (VPG) signal.

7. The apparatus of claim 5, wherein:
the asymmetric window filter comprises a Gaussian-based asymmetric window filter; and
the second filter comprises a Gaussian-based symmetric window filter.

8. The apparatus of claim 5, wherein the processor is further configured to:
apply the first filter to a main frequency of the obtained frequency band spectrum; and
apply the second filter to harmonic frequencies of the obtained frequency band spectrum.

9. The apparatus of claim 5, wherein the processor is further configured to recover the bio-signal by applying an inverse FFT to the frequency band spectrum from which the noise is removed.

10. The apparatus of claim 9, wherein the processor is further configured to:
extract an oscillometric peak from the recovered bio-signal; and
estimate the bio-information based on the extracted oscillometric peak.

11. The apparatus of claim 10, further comprising:
a contact pressure sensor configured to measure contact pressure between the object and the sensor,
wherein the processor is configured to estimate the bio-information based on the oscillometric peak and the measured contact pressure.

12. The apparatus of claim 5, wherein the bio-information comprises at least one of blood pressure, vascular age, arterial stiffness, aortic pressure waveform, vascular compliance, stress index, and fatigue level.

13. A method of estimating bio-information, the method comprising:
obtaining a bio-signal from an object;
obtaining a frequency band spectrum by applying a Fast Fourier Transform (FFT) to the obtained bio-signal;
removing noise from the obtained frequency band spectrum by applying a first filter and a second filter, which are different from each other, to the obtained frequency band spectrum; and
estimating bio-information based on the frequency band spectrum from which the noise is removed;
wherein the first filter comprises an asymmetric window filter.

14. The method of claim 13, wherein:
the first filter comprises a Gaussian-based asymmetric window filter; and
the second filter comprises a Gaussian-based symmetric window filter.

15. The method of claim 13, wherein the removing of the noise comprises:
applying the first filter to a main frequency of the obtained frequency band spectrum; and
applying the second filter to harmonic frequencies of the obtained frequency band spectrum.

16. The method of claim 13, further comprising recovering the bio-signal by applying an inverse FFT to the frequency band spectrum from which the noise is removed.

17. The method of claim 16, wherein the estimating of the bio-information comprises extracting an oscillometric peak from the recovered bio-signal, and estimating the bio-information based on the extracted oscillometric peak.

18. The method of claim 17, further comprising measuring contact pressure applied to the object while the bio-signal is obtained,
wherein the estimating of the bio-information comprises estimating the bio-information based on the oscillometric peak and the measured contact pressure.

19. A method for estimating bio-information from a photoplethysmogram (PPG) signal, the method comprising:
obtaining the PPG signal;
obtaining a frequency band spectrum of the PPG signal based on applying a Fast Fourier Transform (FFT) to the PPG signal;
applying an asymmetric window filter to a main frequency of the frequency band spectrum of the PPG signal;
applying a symmetric window filter to harmonic frequencies of the frequency band spectrum of the PPG signal;
obtaining a noise-removed frequency band spectrum based on applying the asymmetric window filter and the symmetric window filter;
obtaining a noise-removed PPG signal based on applying an inverse FFT to the noise-removed frequency band spectrum;
extracting an oscillometric peak of the noise-removed PPG signal; and
estimating the bio-information based on the oscillometric peak.

20. A signal processing apparatus comprising:
a memory configured to store instructions; and
a processor configured to execute the instructions to:
obtain a signal;
obtain a frequency band spectrum by applying a Fast Fourier Transform (FFT) to the obtained signal; and
remove noise from the obtained frequency band spectrum by applying a first filter and a second filter to the obtained frequency band spectrum,
wherein the first filter has a first shape that is different from a second shape of the second filter.

* * * * *